United States Patent

Fukui et al.

[11] 4,400,508
[45] Aug. 23, 1983

[54] OROTIC ACID DERIVATIVES

[75] Inventors: Kiyoshi Fukui; Noboru Kakeya; Hiroshi Jibiki; Fumio Matsuo, all of Ichihara, Japan

[73] Assignee: UBE Industries, Ltd., Ube, Japan

[21] Appl. No.: 319,793

[22] Filed: Nov. 9, 1981

[30] Foreign Application Priority Data

Nov. 18, 1980 [JP] Japan .............................. 55-161384
Nov. 18, 1980 [JP] Japan .............................. 55-161385

[51] Int. Cl.³ .................. C07D 239/24; C07D 239/30
[52] U.S. Cl. ..................................... 544/313; 544/314
[58] Field of Search ................................ 544/313, 314

[56] References Cited

U.S. PATENT DOCUMENTS 3,118,754 1/1964 Nickell .............................. 544/313
3,352,863 11/1967 Soboczenski .................... 544/313
3,374,083 3/1968 Loux ................................ 544/314

Primary Examiner—Paul M. Coughlan, Jr.
Attorney, Agent, or Firm—Frishauf, Holtz, Goodman & Woodward

[57] ABSTRACT

Novel orotic acid derivatives useful as agricultural chemicals or intermediates thereof are disclosed. The orotic acid derivatives are represented by the formula

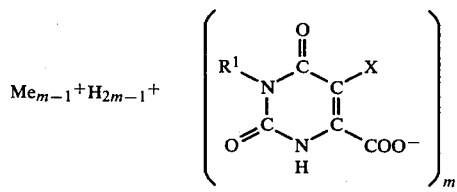

where Me is an alkali metal, $R^1$ is an alkyl group of from 1 to 4 carbon atoms, an allyl group, a cyclohexyl group, a benzyl group, or a group

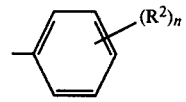

(where $R^2$ is an alkyl group of from 1 to 4 carbon atoms, an alkoxyl group of from 1 to 4 carbon atoms or a halogen atom and n is 0, 1, 2 or 3), m is an integer of 1 or 2, and X is a chlorine, bromine or iodine atom or a group —$COR^0$ (where $R^0$ is an alkyl group of from 1 to 4 carbon atoms or a phenyl group) when m is 1, and a group —$COO^-$ when m is 2.

26 Claims, No Drawings

OROTIC ACID DERIVATIVES

The present invention relates to novel orotic acid derivatives. The orotic acid derivatives of the present invention are useful as either an agricultural chemical or an intermediate thereof.

Namely, the present invention provides a novel orotic acid derivative represented by the general formula

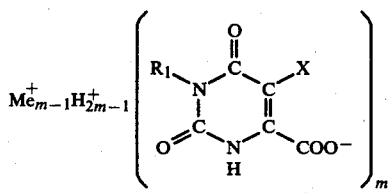

where Me is an alkali metal, $R^1$ is an alkyl group of from 1 to 4 carbon atoms such as methyl, ethyl, propyl and butyl, an allyl group, a cyclohexyl group, a benzyl group or a group

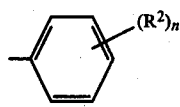

(where $R^2$ is an alkyl group of from 1 to 4 carbon atoms such as methyl, ethyl, propyl and butyl, an alkoxyl group of from 1 to 4 carbon atoms such as methoxy, ethoxy, propoxy and butoxy or a halogen atom and n is an integer of 0, 1, 2 or 3), m is an integer of 1 or 2, and X is a chlorine atom, a bromine atom, an iodine atom or —$COR^0$ (where $R^0$ is an alkyl group of from 1 to 4 carbon atoms or a phenyl group) when m is 1, and a group —$COO^-$ when m is 2.

The general formula I covers an alkali metal salt of 5-carboxyorotic acid represented by the formula

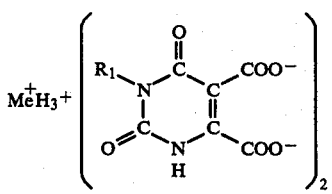

and a 5-halo- or 5-acylorotic acid represented by the formula

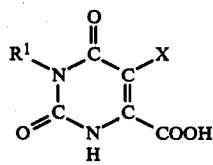

where Me, $R^1$ and X are as defined above.

The alkali metal salt of 5-carboxyorotic acid of the formula II is useful as an intermediate of the 5-haloorotic acid covered by the formula III or as an agricultural chemical. The 5-haloorotic acid and the 5-acylorotic acid represented by the formula III are useful as an agricultural chemical or as an intermediate thereof.

Typical examples of the alkali metal of 5-carboxyorotic acid of the formula II according to the present invention will be given below:

| Compound Nos. | Me | $R^1$ | Melting points (°C.) | Notes |
|---|---|---|---|---|
| 1 | K | iso-$C_3H_7$ | 200–201 (decomp.) | Monohydrate |
| 2 | K | n-$C_4H_9$ | 201–203 (decomp.) | |
| 3 | Na | n-$C_4H_9$ | 205 (decomp.) | Monohydrate |
| 4 | Li | n-$C_4H_9$ | 140–141 | |
| 5 | K | —$CH_2$—CH=$CH_2$ | 196 (decomp.) | Monohydrate |
| 6 | K | —$CH_2$—⟨phenyl⟩ | 200–201 (decomp.) | |
| 7 | K | ⟨cyclohexyl⟩ | 222–223 (decomp.) | Monohydrate |
| 8 | Na | ⟨cyclohexyl⟩ | 218–219 (decomp.) | Monohydrate |
| 9 | K | ⟨phenyl⟩ | 232–234 (decomp.) | Monohydrate |
| 10 | Na | ⟨phenyl⟩ | 217–218 (decomp.) | Monohydrate |
| 11 | Li | ⟨phenyl⟩ | 248–249 (decomp.) | Monohydrate |
| 12 | K | ⟨phenyl⟩—$CH_3$ | 210–213 (decomp.) | |
| 13 | Na | ⟨phenyl⟩—$CH_3$ | 216–218 (decomp.) | |
| 14 | Li | ⟨phenyl⟩—$CH_3$ | 194–196 (decomp.) | |
| 15 | Na | ⟨phenyl⟩—Cl | 237–238 (decomp.) | Monohydrate |
| 16 | K | ⟨2,4-diCl-phenyl⟩ | 203–205 (decomp.) | Monohydrate |
| 17 | K | ⟨3,5-diCl-phenyl⟩ | 211–212 (decomp.) | Monohydrate |
| 18 | Na | ⟨3,5-diCl-phenyl⟩ | 260–261 (decomp.) | |

-continued

| Compound Nos. | Me | R¹ | Melting points (°C.) | Notes |
|---|---|---|---|---|
| 19 | Li | (2,4-dichlorophenyl) | 258–260 (decomp.) | Monohydrate |
| 20 | K | (3,4-dichlorophenyl) | 215–217 (decomp.) | |
| 21 | Na | (4-methoxyphenyl) | 227–229 (decomp.) | Monohydrate |

The alkali metal salt of 5-carboxyorotic acid represented by the formula II, may be prepared, for instance, by the following reactions:

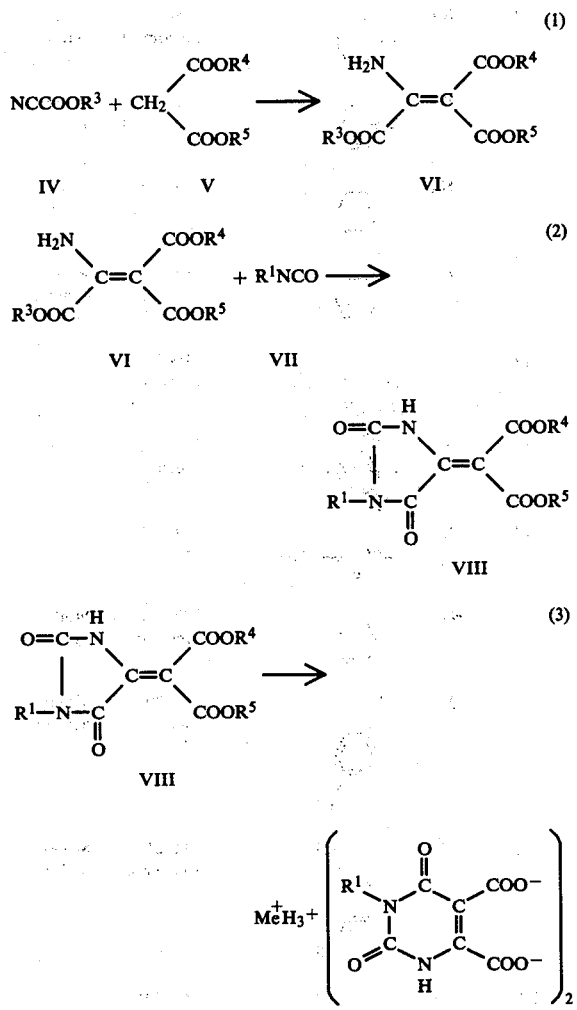

In the above formulas, R¹ is as defined in formula I, and each of R³, R⁴ and R⁵ is an alkyl group of from 1 to 4 carbon atoms such as methyl, ethyl, propyl and butyl.

Reaction represented by the formula (1)

An ester of cyanoformic acid represented by the formula IV and a diester of malonic acid represented by the formula V are reacted in the presence of a titanium or tin halide at a temperature within a range of from $-10°$ to $100°$ C., and the reaction mixture thereby obtained is treated with water or an aqueous acidic solution, whereupon $\alpha,\beta$-unsaturated $\alpha$-amino acid ester represented by the formula VI is obtainable. The amount of the diester of malonic acid is at least an equimolar amount relative to the ester of cyanoformic acid. The titanium or tin halide is sufficient if it is used in an amount of about one mole per mole of the ester of cyanoformic acid. The reaction may be carried out in the presence or absence of a solvent such as an aromatic hydrocarbon or a halogenated hydrocarbon.

Reaction represented by the formula (2)

The $\alpha,\beta$-unsaturated $\alpha$-amino acid ester represented by the formula VI and an isocyanate represented by the formula VII are reacted in the presence of quaternary ammonium fluoride, or such fluoride plus a tertiary amine, at a temperature within a range of from $20°$ to $100°$ C., whereupon a hydantoin derivative represented by the formula VIII is obtainable. In this reaction, it is preferred to use a reaction solvent such as an aromatic hydrocarbon, a halogenated hydrocarbon or an ether. The amounts of the isocyanate and the quaternary ammonium fluoride are preferably from 2 to 3 moles and from 0.1 to 1 mole, respectively, relative to one mole of the $\alpha,\beta$-unsaturated $\alpha$-amino acid ester.

Reaction represented by the formula (3)

The hydantoin derivative represented by the formula VIII is reacted with an alkali hydroxide in water, an alcohol or a mixed solvent thereof, at room temperature or at an elevated temperature, and a mineral acid is then added to the reaction mixture, whereupon the metal salt of 5-carboxyorotic acid represented by the formula II is obtainable. As the alkali hydroxide, sodium hydroxide, potassium hydroxide or lithium hydroxide is preferably used, and its amount is preferably from 3 to 5 moles per mole of the hydantoin derivative. The desired alkali metal salt of 5-carboxyorotic acid can be isolated from the reaction mixture by an isolation method known per se.

The 5-haloorotic acid represented by the formula III where X is a chlorine atom, a bromine atom or an iodine atom, is prepared by reacting the alkali metal salt of 5-carboxyorotic acid of the formula II with a halogenating agent.

As the halogenating agent, there may be mentioned a halogen such as chlorine, bromine or iodine; a hypohalogeneous acid such as hypochlorous acid, hypobromous acid or hypoiodous acid; or its alkali metal salts; and an N-haloimide such as N-chlorosuccinimide, N-bromosuccinimide or N-bromophthalimide.

The amount of the halogenating agent is preferably within a range of from 2 to 2.5 moles per mole of the alkali metal salt of 5-carboxyorotic acid.

The reaction of the alkali metal salt of 5-carboxyorotic acid with the halogenating agent is preferably conducted in water as the reaction solvent. In some cases, a combination of water with an appropriate solvent inert to the reaction may be used. As such an inert solvent, benzene, chlorobenzene, dichlorobenzene or carbon tetrachloride may be mentioned.

The reaction may be carried out by any method so long as the alkali metal salt of 5-carboxyorotic acid and the halogenating agent are thereby contacted at a predetermined temperature for a predetermined period of time. As a method for contacting these starting materials, a method is usually employed in which the halogenating agent is added directly or in a form of a solution in water or the above mentioned inert organic solvent, to an aqueous solution or suspension of the alkali metal salt of 5-carboxyorotic acid.

The reaction of the alkali metal salt of 5-carboxyorotic acid with the halogenating agent can be facilitated by an addition of an alkali metal hydroxide to the reaction system, whereby the yield of the desired 5-haloorotic acid can be improved. Therefore, it is preferred to add to the reaction system an alkali metal hydroxide in an amount of from 1 to 3 moles per mole of the alkali metal salt of 5-carboxyorotic acid.

As mentioned above, the alkali metal salt of 5-carboxyorotic acid of the formula II is prepared by reacting a 5-bis(alkoxycarbonyl)methylene hydantoin of the formula VIII with an alkali metal hydroxide in water at room temperature or at an elevated temperature, and then adding a mineral acid to the reaction mixture thereby obtained. The reaction mixture obtained by the above method or the reaction mixture prior to the treatment with the mineral acid, may directly be subjected to the halogenation for the production of the 5-haloorotic acid of the formula III.

If the reaction temperature is excessively high, the yield of the desired product tends to decrease. Normally, it is preferred that the reaction temperature is within a range of from 0° to 100° C.

The reaction can usually be completed within a period of from 1 to 25 hours.

Most of the desired 5-haloorotic acids are crystals hardly soluble in water. Accordingly, they can be isolated by filtering the reaction mixture. In case the 5-haloorotic acid is dissolved in water, it can be isolated by removing water or the solvent from the reaction mixture by means of a known method such as distillation and extracting it from the residue thereby obtained, by means of an organic solvent. Further, in a case where the reaction of the alkali metal salt of 5-carboxyorotic acid and the halogenating agent is carried out with an addition of an alkali metal hydroxide, it is possible to isolate the 5-haloorotic acid by conducting the above mentioned operation after adding a mineral acid such as hydrochloric acid or sulfuric acid to the reaction mixture, in an amount corresponding stoichiometrically to the alkali metal hydroxide used.

Specific examples of the 5-haloorotic acid of the formula III according to the present invention will be given below.

| Compound Nos. | $R^1$ | X | Decomposition point (°C.) | Notes |
|---|---|---|---|---|
| 22 | —CH(CH₃)₂ | Cl | 241–242 | Monohydrate |
| 23 | —C₆H₅ | " | 242–243 | Monohydrate |
| 24 | —C₆H₄—OCH₃ | " | 236 | |
| 25 | —C₆H₄—Cl | " | 233–234 | Monohydrate |
| 26 | —CH(CH₃)₂ | Br | 248–249 | adduct with ½ mole of CH₃CN |
| 27 | —CH₂CH₂CH₂CH₃ | " | 218–219 | Monohydrate |
| 28 | —CH₂—C₆H₅ | " | 255–256 | |
| 29 | —C₆H₅ | " | 260–262 | Monohydrate |
| 30 | —C₆H₄—CH₃ | " | 242 | Monoethanol adduct |
| 31 | —C₆H₄—OCH₃ | " | 266–268 | Monoethanol adduct |
| 32 | —C₆H₄—Cl | " | 235–237 | Monohydrate |
| 33 | —C₆H₃(Cl)₂ (3,5-dichlorophenyl) | " | 230–232 | Monoethanol adduct |
| 34 | —CH(CH₃)₂ | I | 242–244 | Monoethanol adduct |
| 35 | —C₆H₅ (H-substituted) | " | 239–240 | Monoethanol adduct |
| 36 | —CH₂—CH=CH₂ | " | 185–186 | ½ hydrate |
| 37 | —C₆H₅ | " | 258–260 | Monoethanol adduct |
| 38 | —C₆H₄—OCH₃ | " | 263 | Monoethanol adduct |
| 39 | —C₆H₄—Cl | " | 268–270 | |

The 5-acylorotic acid represented by the formula III where X is —COR⁰, may be prepared, for instance, by the following reactions.

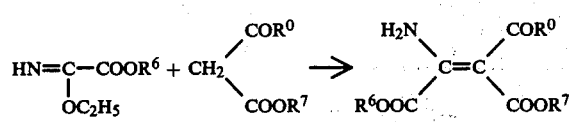

(4)

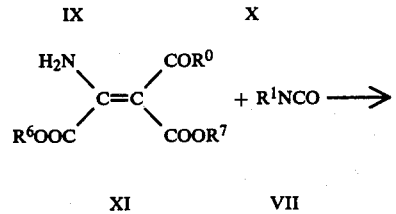

(5)

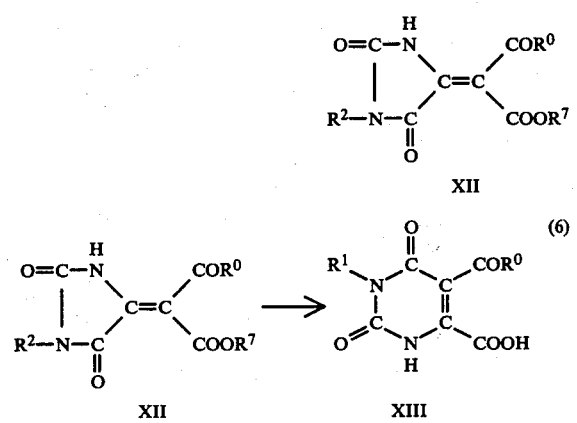

(6)

In the above formulas, $R^0$ and $R^1$ are as defined above, and each of $R^6$ and $R^7$ is an alkyl group of from 1 to 4 carbon atoms such as methyl, ethyl, propyl and butyl.

Reaction represented by the formula (4)

An ester of ethoxyiminoacetic acid represented by the formula IX and an activated methylene compound of the formula X are reacted within a temperature range of from 10° to 150° C. to produce an α,β-unsaturated α-amino acid ester. To attain good yield, it is preferred that the activated methylene compound is used at least in an equimolar amount relative to the ester of ethoxyiminoacetic acid so that the activated methylene compound serves by itself as a reaction solvent.

Reaction represented by the formula (5)

The α,β-unsaturated α-amino acid ester represented by the formula XI and an isocyanate represented by the formula VII are reacted in the presence of quaternary ammonium fluoride within a temperature range of from 20° to 100° C. to produce a hydantoin derivative represented by the formula XII. For this reaction, it is preferred that an aromatic hydrocarbon, a halogenated hydrocarbon or an ether is used as a reaction solvent. The isocyanate and the quaternary ammonium fluoride are used in amounts of from 2 to 3 moles and from 0.1 to 1 mole, respectively, per mole of the α,β-unsaturated α-amino acid ester.

Reaction represented by the formula (6)

The hydantoin derivative represented by the formula XII is reacted with an alkali metal hydroxide at room temperature or at an elevated temperature in water, an alcohol or a mixed solvent thereof, and then the reaction mixture thereby obtained, is neutralized by an acid, whereupon the 5-acylorotic acid represented by the formula XIII is obtained. As the alkali metal hydroxide, sodium hydroxide, potassium hydroxide or lithium hydroxide is preferably used. Its amount is preferably from 2 to 5 moles per mole of the hydantoin derivative. The desired 5-acylorotic acid can be isolated from the reaction mixture by a method known per se.

Typical examples of the 5-acylorotic acid of the present invention will be given below:

| Compound Nos. | $R^0$ | $R^1$ | Melting points (°C.) | Notes |
|---|---|---|---|---|
| 40 | —C₆H₅ (phenyl) | —CH₃ | 214–216 (decomp.) | Monohydrate |
| 41 | " | —CH(CH₃)₂ | 203–204 (decomp.) | |
| 42 | " | —CH₂CH₂CH₂CH₃ | 196–198 (decomp.) | |
| 43 | " | —CH₂—CH=CH₂ | 204–206 (decomp.) | |
| 44 | " | —C₆H₁₁ (cyclohexyl) | 183–184 (decomp.) | Monohydrate |
| 45 | " | —CH₂—C₆H₅ | 198–199 (decomp.) | |
| 46 | " | —C₆H₅ | 208–208.5 (decomp.) | Monohydrate |
| 47 | " | —C₆H₄—CH₃ | 222–224 (decomp.) | Monoethanol adduct |
| 48 | " | —C₆H₃(CH₃)₂ | 218–220 (decomp.) | Monoethanol adduct |
| 49 | " | —C₆H₃Cl₂ | 219–220 (decomp.) | Monoethanol adduct |
| 50 | " | —C₆H₃Cl₂ | 201–203 (decomp.) | Monoisopropanol adduct |
| 51 | " | —C₆H₄—OCH₃ | 196–197 (decomp.) | Monohydrate |
| 52 | —CH₃ | —CH₂CH₃ | 184–185 (decomp.) | |
| 53 | " | —CH₂CH₂CH₂CH₃ | 149–152 | |
| 54 | " | —C₆H₁₁ (cyclohexyl) | 223–224 (decomp.) | Monohydrate |
| 55 | " | —C₆H₅ | 232–234 (decomp.) | Monohydrate |

-continued

| Compound Nos. | $R^0$ | $R^1$ | Melting points (°C.) | Notes |
|---|---|---|---|---|
| 56 | " | —⟨phenyl⟩—CH₃ | 224–226 (decomp.) | |
| 57 | " | —⟨phenyl⟩—Cl | 193–195 (decomp.) | |
| 58 | " | —⟨phenyl⟩ with Cl, Cl | 247 (decomp.) | Mono-ethanol adduct |
| 59 | " | —⟨phenyl⟩—OCH₃ | 178–179 (decomp.) | Mono-ethanol adduct |

Now, Examples for the preparation of the alkali metal salts of 5-carboxyorotic acids will be given.

Example 1 (Compd. No. 2)

Added successively and dropwise to 100 ml of 1,2-dichloroethane containing 108.7 millimoles of tin tetrachloride, were 60 ml of benzene containing 108.7 millimoles of diethylmalonate, and 60 ml of benzene containing 108.7 millimoles of ethyl cyanoformate, and the reaction was conducted for one hour under reflux. Under ice-cooling, 100 ml of water was dropwise added to the reaction mixture, and then stirred for one hour. After separation of the reaction mixture, the aqueous layer thereby obtained was extracted three times each with 40 ml of chloroform. The extracted solution was added to the organic layer, and the solution thereby obtained was dried over anhydrous sodium sulfate, and then concentrated under reduced pressure. To the residue, 50 ml of n-hexane was added, and then filtered, whereupon 26.71 g of crystals of 1-amino-1,2,2-tris(ethoxycarbonyl)ethylene (hereinafter referred to simply as "ATE") were obtained. They were recrystallized from diisopropyl ether, whereupon 18.52 g of colourless prisms having a melting point of from 69.5° to 70° C. were obtained.

To 80 ml of 1,2-dichloroethane containing 4.6 millimoles of tetraethylammonium fluoride and 20.0 millimoles of ATE, 50.0 millimoles of triethylamine was added and then, 20 ml of 1,2-dichloroethane containing 50.0 millimoles of n-butyl isocyanate was dropwise added. Then, the reaction was conducted for one hour at room temperature with stirring. The reaction mixture thereby obtained was washed with 50 ml of water, then dried over anhydrous sodium sulfate, and concentrated under reduced pressure. The residue was distilled under reduced pressure, whereupon 1.12 g of ethyl N-(n-butyl)carbamate acid (boiling point: 73° C./3.5 mmHg) was obtained as the distillate. The distillation residue was recrystallized from n-hexane, whereupon 5.02 g of crystals (melting point: from 59° to 61° C.) of 5-bis(ethoxycarbonyl)methylene-3-(n-butyl)hydantoin were obtained.

To 30 ml of ethanol containing 10.5 millimoles of 5-bis(ethoxycarbonyl)methylene-3-(n-butyl)hydantoin, 10 ml of water containing 42 millimoles of potassium hydroxide was added at room temperature, and the reaction was conducted for 2 hours under reflux. To the reaction mixture, 42 ml of 1 N hydrochloric acid was added under ice-cooling, and then filtered, whereupon 1.8 g of crystals of potassium 5-carboxy-1-(n-butyl)orotate were obtained. They were recrystallized from 80 ml of a mixed solvent comprising 1 part by volume of water and 3 parts by volume of ethanol, whereupon 1.13 g of colourless needles having a decomposition point of from 201° to 203° C. were obtained. The results obtained by the elemental analysis thereof are shown below.

| | C | H | N |
|---|---|---|---|
| Analytical value | 43.75 | 4.14 | 10.27 |
| Calculated value (As $C_{20}H_{23}N_4O_{12}K$) | 43.64 | 4.21 | 10.18 |

Example 2 (Compd. No. 6)

To 50 ml of 1,2-dichloroethane containing 10.0 millimoles of ATE prepared in a manner similar to Example 1 and 2.5 millimoles of tetraethylammonium fluoride, 20 ml of 1,2-dichloroethane containing 25.0 millimoles of benzyl isocyanate was added dropwise at room temp temperature, and then 20.0 millimoles of triethylamine was added. Then, the reaction was carried out for one hour under reflux. The reaction mixture was concentrated under reduced pressure, and 50 ml of isopropanol was added to the residue, and then filtered, whereupon 1.96 g of colourless needles (melting point: from 149° to 151° C.) of 5-bis(ethoxycarbonyl)methylene-3-benzylhydantoin was obtained.

To 25 ml of ethanol containing 3.1 millimoles of 5-bis-(ethoxycarbonyl)methylene-3-benzylhydantoin, 25 ml of water containing 12.6 millimoles of potassium hydroxide was added at room temperature, and reacted for 2 hours under reflux. The reaction mixture was concentrated under reduced pressure, and the residue was dissolved in 20 ml of water to obtain a solution, which was then added to a mixed solution comprising 11 ml of 1 N sulfuric acid and 60 ml of water and then filtered, whereupon 0.73 g of crystals of potassium 5-carboxy-1-benzylorotate, were obtained. They were recrystallized from water, whereupon 0.37 g of colourless needles having a decomposition point of from 200° to 201° C. were obtained. The results of their elemental analysis are as follows:

| | C | H | N |
|---|---|---|---|
| Analytical value | 50.61 | 3.08 | 8.97 |
| Calculated value (As $C_{26}H_{19}N_4O_{12}K$) | 50.49 | 3.10 | 9.06 |

Example 3 (Compd. No. 10)

To 60 ml of 1,2-dichloroethane containing 42.4 millimoles of ATE prepared in a manner similar to Example 1 and 8.6 millimoles of tetra(n-butyl)ammonium fluoride, 40 ml of 1,2-dichloroethane containing 101.8 millimoles of phenyl isocyanate was dropwise added at room temperature, and the reaction was conducted for one hour under reflux. The reaction mixture was concentrated under reduced pressure, and the residue was recrystallized from ethanol, whereupon 12.14 g of colourless crystals (melting point: 167° C.) of 5-bis(ethoxycarbonyl)methylene-3-phenylhydantoin were obtained.

To 30 ml of ethanol containing 9.0 millimoles of 5-bis(ethoxycarbonyl)methylene-3-phenylhydantoin, 20 ml of water containing 36.1 millimoles of sodium hydroxide was added under reflux, and then the reaction was conducted for one hour. To the reaction mixture, 40 ml of 1 N hydrochloric acid was added under ice-cooling, and then filtered, whereupon 2.53 g of crystals of sodium 5-carboxy-1-phenylorotate were obtained. They were recrystallized from water, whereupon 1.00 g of colourless crystals having a decomposition point of from 217° to 218° C. were obtained. From the following results of their elemental analysis, these crystals were confirmed to be a monohydrate of sodium 5-carboxy-1-phenylorotate.

|  | C | H | N |
|---|---|---|---|
| Analytical value | 48.65 | 2.99 | 9.45 |
| Calculated value (As $C_{24}H_{17}N_4O_{13}Na$) | 48.66 | 2.89 | 9.46 |

Example 4 (Compd. No. 14)

To 80 ml of 1,2-dichloroethane containing 20.0 millimoles of ATE prepared in a manner similar to Example 1 and 3.8 millimoles of tetraethylammonium fluoride, 20 ml of 1,2-dichloroethane containing 50.0 millimoles of p-tolyl isocyanate was dropwise added, and the reaction was conducted under reflux for 3 hours. The reaction mixture was concentrated under reduced pressure, and 50 ml of diisopropyl ether was added to the residue and filtered, whereupon 6.59 g of crystals of 5-bis(ethoxycarbonyl)methylene-3-(p-tolyl)hydantoin were obtained. They were recrystallized from ethanol, whereupon 4.67 g of colourless needles having a melting point of from 154° to 155° C. were obtained.

To 30 ml of ethanol containing 7.2 millimoles of 5-bis(ethoxycarbonyl)methylene-3-(p-tolyl)hydantoin, 10 ml of water containing 28.8 millimoles of lithium hydroxide was added at room temperature, and then reaction was conducted for one hour under reflux. The reaction mixture was concentrated under reduced pressure, and 20 ml of water was added to the residue, and filtered, whereupon 0.05 g of crystals of N,N'-di(p-tolyl)urea were obtained. The filtrate was added to 20 ml of 6 N sulfuric acid, and filtered, whereupon 1.61 g of crystals of lithium 5-carboxyl-1-(p-tolyl)orotate were obtained. These crystals were recrystallized from water, whereupon 0.63 g of colourless crystals having a decomposition point of from 194° to 196° C. were obtained. The results of their elemental analysis are as follows:

|  | C | H | N |
|---|---|---|---|
| Analytical value | 53.67 | 3.55 | 9.54 |
| Calculated value (As $C_{26}H_{19}N_4O_{12}Li$) | 53.26 | 3.27 | 9.55 |

Example 5 (Compd. No. 15)

To 80 ml of 1,2-dichloroethane containing 20.0 millimoles of ATE prepared in a manner similar to Example 1 and 4.2 millimoles of benzyltrimethylammonium fluoride, 20 ml of 1,2-dichloroethane containing 50.7 millimoles of p-chlorophenyl isocyanate was dropwise added at room temperature, and the reaction was conducted for 2 hours under reflux. The reaction mixture was concentrated under reduced pressure, and 30 ml of ethanol was added to the residue, and filtered, whereupon 6.89 g of crystals of 5-bis(ethoxycarbonyl)methylene-3-(p-chlorophenyl)hydantoin were obtained. These crystals were recrystallized from ethanol, whereupon 5.50 g of colourless needles having a melting point of from 161.5° to 162° C. were obtained.

To 30 ml of ethanol containing 12.3 millimoles of 5-bis(ethoxycarbonyl)methylene-3-(p-chlorophenyl)hydantoin, 10 ml of water containing 49.0 millimoles of sodium hydroxide was added at room temperature, and the reaction was conducted for one hour under reflux. The reaction mixture was concentrated under reduced pressure, and 10 ml of water was added to the residue and filtered, whereupon 0.28 g of crystals of N,N'-di(p-chlorophenyl)urea were obtained. The filtrate was added to 49 ml of 1 N hydrochloric acid, and then filtered, 3.38 g of crystals of sodium 5-carboxy-1-(p-chlorophenyl)ororate were obtained. These crystals were recrystallized from water, whereupon 2.35 g of colourless crystals having a decomposition point of from 237° to 238° C. were obtained. From the following results of their elemental analysis, these crystals were confirmed to be a monohydrate of sodium 5-carboxyl-1(p-chlorophenyl)orotate.

|  | C | H | N | Cl |
|---|---|---|---|---|
| Analytical value | 43.70 | 2.03 | 8.53 | 11.07 |
| Calculated value (As $C_{24}H_{15}Cl_2N_4O_{13}Na$) | 43.60 | 2.29 | 8.47 | 10.72 |

Now, Examples for the preparation of the 5-haloorotic acids will be given. In these Examples, the yield of the 5-haloorotic acid is based on the amount of the alkali metal salt of 5-carboxyorotic acid used.

Example 6 (Compd. No. 22)

To 30 ml of water containing 1.5 g of sodium 5-carboxy-1-isopropylorotate monohydrate, 30 ml of carbon tetrachloride containing 0.46 g of chlorine was dropwise added at room temperature, whereupon 20 ml of gas was generated. The mixture was heated and reacted for one hour under reflux.

After the reaction, the reaction mixture was filtered, whereupon 0.25 g (yield: 17%) of crystals of 5-chloro-1-isopropylorotic acid monohydrate were obtained. They were recrystallized from water, whereupon colourless crystals having a decomposition point of from 241° to 242° C. were obtained. The results of their elemental analysis are as follows:

|  | C | H | N | Cl |
|---|---|---|---|---|
| Analytical value: | 38.30 | 4.34 | 11.09 | 13.80 |
| Calculated value: (As $C_8H_{11}ClN_2O_5$) | 38.34 | 4.42 | 11.18 | 14.14 |

Example 7 (Compd. No. 22)

To 50 ml of water containing 2.62 g of sodium 5-carboxy-1-isopropylorotate monohydrate, 15 ml of 1 N sodium hydroxide was added, and then 7.44 g of an aqueous solution containing 12% by weight of sodium hypochlorite was added. The mixture was heated and reacted for one hour under reflux.

After the reaction, 40 ml of 1 N hydrochloric acid was dropwise added to the reaction mixture at room temperature, whereupon 130 ml of gas was generated.

The mixture was filtered, whereupon 0.44 g (yield: 18%) of crystals of 5-chloro-1-isopropylorotic acid monohydrate were obtained. The filtrate was concentrated under reduced pressure, and 10 ml of water was added to the residue and filtered, whereupon 0.52 g (yield: 21%) of crystals of 5-chloro-1-isopropylorotic acid monohydrate are additionally obtained.

Example 8 (Compd. No. 23)

To 90 ml of water containing 1.53 g of sodium 5-carboxy-1-phenylorotate monohydrate, 10 ml of carbon tetrachloride containing 0.44 g of chlorine was dropwise added at room temperature, whereupon 97.5 ml of gas was generated. The mixture was reacted at room temperature for 20 hours with stirring.

After the reaction, the reaction mixture was filtered, whereupon 0.38 g (yield: 26%) of crystals of 5-chloro-1-phenylorotic acid monohydrate were obtained. They were recrystallized from water, whereupon colourless needles having a decomposition point of from 242° to 243° C. were obtained. The reults of their elemental analysis are as follows:

|  | C | H | N | Cl |
|---|---|---|---|---|
| Analytical value: | 46.54 | 3.17 | 9.54 | 12.14 |
| Calculated value: (As $C_{11}H_9ClN_2O_5$) | 46.41 | 3.19 | 9.84 | 12.45 |

Example 9 (Compd. No. 24)

To 60 ml of water containing 3.26 g of sodium 1-(p-methoxyphenyl)-5-carboxyorotate monohydrate, 15 ml of 1 N sodium hydroxide was added at room temperature and then 7.44 g of an aqueous solution containing 12% by weight of sodium hypochlorite, was added. The mixture was heated and reacted for one hour under reflux.

After the reaction, 40 ml of 1 N hydrochloric acid was dropwise added at room temperature to the reaction mixture thereby obtained, whereupon 153 ml of gas was generated. The mixture was filtered, whereupon 1.54 g (yield: 52%) of crystals of 1-(p-methoxyphenol)-5-chloroorotic acid were obtained. They were recrystallized from ethanol, whereupon yellowish needles having a decomposition point of 236° C. were obtained. The results of their elemental analysis are as follows:

|  | C | H | N | Cl |
|---|---|---|---|---|
| Analytical value: | 48.97 | 3.12 | 9.42 | 11.68 |
| Calculated value: (As $C_{12}H_9ClN_2O_5$) | 48.58 | 3.06 | 9.44 | 11.95 |

Example 10 (Compd. No. 25)

To 90 ml of water containing 1.83 g of sodium 5-carboxy-1-(p-chlorophenyl)orotate monohydrate, 10 ml of carbon tetrachloride containing 0.47 g of chlorine was dropwise added at room temperature, whereupon 77.5 ml of gas was generated. The mixture was reacted for a day with stirring.

After the reaction, the reaction mixture thereby obtained was filtered, whereupon 0.70 g of crystals were obtained. They were added to 50 ml of ethanol, and filtered while they were hot. The filtrate was concentrated under reduced pressure, whereupon 0.42 g (yield: 25%) of crystals of 5-chloro-1-(p-chlorophenyl)orotic acid were obtained. They were recrystallized from water, whereupon colourless crystals having a decomposition point of from 233° to 234° C. were obtained as an adduct with water in a molar ratio of 1:1. The results of their elemental analysis are as follows:

|  | C | H | N | Cl |
|---|---|---|---|---|
| Analytical value: | 41.65 | 2.36 | 8.76 | 21.54 |
| Calculated value: (As $C_{11}H_8Cl_2N_2O_5$) | 41.40 | 2.53 | 8.78 | 22.22 |

Example 11 (Compd. No. 25)

To 50 ml of water containing 1.65 g of sodium 5-carboxy-(p-chlorophenyl)orotate monohydrate, 7.5 ml of 1 N sodium hydroxide was added at room temperature, and then 3.71 g of an aqueous solution containing 12% by weight of sodium hypochlorite was added. The mixture was heated and reacted for one hour under reflux.

After the reaction, 10 ml of 2 N hydrochloric acid was dropwise added to the reaction mixture thereby obtained, at room temperature, whereupon 65 ml of gas was generated. The mixture was filtered, whereupon 0.97 g (yield: 61%) of crystals of 5-chloro-1-(p-chlorophenyl)orotic acid monohydrate were obtained.

Example 12 (Compd. No. 26)

To 80 ml of water containing 2.14 g of sodium 5-carboxy-1-isopropylorotate monohydrate, 20 ml of carbon tetrachloride containing 1.38 g of bromine was dropwise added at room temperature, whereupon 130 ml of gas was generated. The mixture was heated and reacted for 7 hours at 60° C.

After the reaction, the reaction mixture thereby obtained was filtered, whereupon 1.26 g (yield: 56%) of crystals of 5-chloro-1-isopropylorotic acid were obtained. They were recrystallized from acetonitrile, whereupon colourless crystals having a decomposition point of from 248° to 249° C. were obtained as an adduct with ½ acetonitrile. The results of their elemental analysis are as follows:

|  | C | H | N | Br |
|---|---|---|---|---|
| Analytical value: | 36.47 | 3.75 | 12.19 | 27.33 |
| Calculated value: (As $C_8H_9BrN_2O_4 \cdot \frac{1}{2}CH_3CN$) | 36.32 | 3.56 | 11.77 | 26.84 |

Example 13 (Compd. No. 27)

To 25 ml of water containing 0.74 g of sodium 1-(n-butyl)-5-carboxyorotate monohydrate, 10 ml of water containing 0.43 g of bromine was added under ice-cooling, whereupon 45 ml of gas was generated. The mixture was reacted for 20 hours with stirring at room temperature.

After the reaction, the reaction mixture thereby obtained was filtered, whereupon 0.29 g (yield: 35%) of crystals of 5-bromo-1-(n-butyl)orotic acid monohydrate were obtained. They were recrystallized from water, whereupon yellowish bulky crystals having a decomposition point of from 218° to 219° C. were obtained. The results of their elemental analysis are as follows:

|  | C | H | N | Br |
|---|---|---|---|---|
| Analytical value: | 35.08 | 4.03 | 9.05 | 25.92 |
| Calculated value: | 34.97 | 4.24 | 9.06 | 25.85 |

|   | C | H | N | Br |
|---|---|---|---|---|
| (As C₉H₁₃BrN₂O₅) | | | | |

The filtrate was concentrated under reduced pressure, and 5 ml of water was added to the residue and filtered, whereupon 0.1 g (yield: 12%) of 5-bromo-1-(n-butyl)orotic acid monohydrate was additionally obtained.

Example 14 (Compd. No. 28)

To 100 ml of water containing 2.15 g of sodium 1-benzyl-5-carboxyorotate monohydrate, 20 ml of water containing 1.35 g of bromine was dropwise added under ice-cooling, whereupon 360 ml of gas was generated. The mixture was reacted for 5 hours at room temperature with stirring.

After the reaction, the reaction mixture thereby obtained, was filtered, whereupon 1.42 g (yield: 63%) of crystals of 1-benzyl-5-bromoorotic acid were obtained. They were recrystallized from ethanol, whereupon orange blocks having a decomposition point of from 255° to 256° C. were obtained. The results of their elemental analysis are as follows:

|   | C | H | N | Br |
|---|---|---|---|---|
| Analytical value: | 44.56 | 2.86 | 8.44 | 24.78 |
| Calculated value: | 44.32 | 2.79 | 8.61 | 24.57 |
| (As C₁₂H₉BrN₂O₄) | | | | |

Example 15 (Compd. No. 29)

To 100 ml of water containing 1.6 g of potassium 5-carboxy-1-phenylorotate monohydrate, 0.88 g of N-bromosuccinimide was added at room temperature, and the mixture was then stirred, whereupon 230 ml of gas was generated. The mixture was reacted for 1.5 hours at room temperature with stirring.

After the reaction, the reaction mixture thereby obtained was filtered. To the filtrate, 1 ml of concentrated sulfuric acid was added, and the crystals thereby separated were filtered, whereupon 0.22 g (yield: 13%) of crystals of 5-bromo-1-phenylorotic acid monohydrate were obtained. They were recrystallized from ethanol, whereupon colourless needles having a decomposition point of from 260° to 262° C. were obtained. The results of their elemental are as follows:

|   | C | H | N | Br |
|---|---|---|---|---|
| Analytical value: | 40.33 | 2.73 | 8.35 | 24.51 |
| Calculated value: | 40.14 | 2.75 | 8.51 | 24.30 |
| (As C₁₁H₉BrN₂O₅) | | | | |

Example 16 (Compd. No. 29)

To 50 ml of water containing 1.48 g of sodium 5-carboxy-1-phenylorotate monohydrate, 10 ml of water containing 0.94 g of bromine was dropwise added under ice-cooling. The mixture was reacted for one hour at room temperature with stirring.

After the reaction, the reaction product thereby obtained, was filtered, whereupon 1 g (yield: 61%) of 5-bromo-1-phenylorotic acid monohydrate was obtained.

Example 17 (Compd. No. 30)

To 30 ml of water containing 1.39 g of potassium 5-carboxy-1-(p-tolyl)orotate monohydrate, 0.81 g of N-bromosuccinimide was added at room temperature, and then the mixture was stirred at room temperature, whereupon 92 ml of gas was generated. The mixture was heated and reacted for 15 minutes under reflux.

After the reaction, the reaction mixture thereby obtained was filtered. The filtrate was concentrated under reduced pressure, and 10 ml of water was added to the residue and filtered, whereupon 0.54 g (yield: 38%) of crystals of 5-bromo-1-(p-tolyl)orotic acid were obtained. They were recrystallized from ethanol, whereupon colourless crystals having a decomposition point of 242° C. were obtained as an adduct with ethanol in a molar ratio of 1:1. The results of their elemental analysis are as follows:

|   | C | H | N | Br |
|---|---|---|---|---|
| Analytical value: | 45.30 | 4.08 | 7.53 | 21.46 |
| Calculated value: | 45.30 | 4.07 | 7.55 | 21.53 |
| (As C₁₄H₁₅BrN₂O₅) | | | | |

Example 18 (Compd. No. 30)

To 50 ml of water containing 0.64 g of potassium 5-carboxy-1-(p-tolyl)orotate monohydrate, 10 ml of water containing 0.43 g of bromine was dropwise added under ice-cooling. The mixture was reacted for 20 hours at room temperature with stirring. During this reaction, 35 ml of gas was generated.

After the reaction, the reaction mixture was filtered, whereupon 0.19 g (yield: 29%) of crystals of 5-bromo-1-(p-tolyl)orotic acid were obtained.

Example 19 (Compd. No. 31)

To 80 ml of water containing 1.74 g of sodium 1-(p-methoxyphenyl)-5-carboxyorotate monohydrate, 20 ml of water containing 0.85 g of bromine was dropwise added at room temperature, whereupon 58 ml of gas was generated. The mixture was stirred at room temperature and reacted for one day.

After the reaction, the reaction mixture thereby obtained was filtered, whereupon 0.94 g (yield: 52%) of crystals of 1-(p-methoxyphenyl)-5-bromoorotic acid were obtained. They were recrystallized from ethanol, whereupon yellow needles having a decomposition point of from 266° to 268° C. were obtained as an adduct with ethanol in a molar ratio of 1:1. The results of their elemental analysis are as follows:

|   | C | H | N |
|---|---|---|---|
| Analytical value: | 43.80 | 3.85 | 7.05 |
| Calculated value: | 43.43 | 3.90 | 7.24 |
| (As C₁₄H₁₅BrN₂O₆) | | | |

Example 20 (Compd. No. 32)

To 50 ml of water containing 1.33 g of potassium 5-carboxy-1-(p-chlorophenyl)orotate monohydrate, 10 ml of water containing 0.63 g of bromine was added under ice-cooling, and the mixture was reacted for 20 hours at room temperature with stirring. During the reaction, 45 ml of gas was generated.

After the reaction, the reaction mixture thereby obtained, was filtered, whereupon 1.08 g (yield: 76%) of crystals of 5-bromo-1-(p-chlorophenyl)orotic acid monohydrate were obtained. They were recrystallized from water, whereupon light orange blocks having a decomposition point of from 235° to 237° C. were obtained. The results of their elemental analysis are as follows:

|  | C | H | N |
|---|---|---|---|
| Analytical value: | 36.79 | 2.45 | 7.78 |
| Calculated value: (As $C_{11}H_8BrClN_2O_5$) | 36.34 | 2.22 | 7.71 |

Example 21 (Compd. No. 33)

To 70 ml of water containing 1.8 g of sodium 5-carboxy-1-(3,5-dichlorophenyl)orotate monohydrate, 10 ml of water containing 1.09 g of bromine was dropwise added under ice-cooling, and then the mixture was reacted at room temperature for 18 hours with stirring. During the reaction, 190 ml of gas was generated.

After the reaction, the reaction mixture thereby obtained was filtered, whereupon 1.98 g (yield: 76%) of crystals of 5-bromo-1-(3,5-dichlorophenyl)orotic acid were obtained. They were recrystallized from ethanol, whereupon colourless needles having a decomposition point of from 230° to 232° C. were obtained as an adduct with ethanol in a molar ratio of 1:1. The results of their elemental analysis are as follows:

|  | C | H | N |
|---|---|---|---|
| Analytical value: | 36.27 | 2.44 | 6.51 |
| Calculated value: (As $C_{13}H_{11}BrCl_2N_2O_5$) | 36.65 | 2.60 | 6.58 |

Example 22 (Compd. No. 34)

To 50 ml of water containing 1.31 g of sodium 5-carboxy-1-isopropylorotate monohydrate, 17.5 ml of 1 N sodium hydroxide was added at room temperature, and then 1.27 g of iodine was added. The mixture was heated and reacted for 2.5 hours under reflux.

After the reaction, 10 ml of 2 N hydrochloric acid was added to the reaction mixture thereby obtained, and filtered, whereupon 0.79 g (yield: 49%) of crystals of 5-iodo-1-isopropylorotic acid were obtained. They were recrystallized from ethanol, whereupon colourless needles having a decomposition point of from 242° to 244° C. were obtained as an adduct with ethanol in a molar ratio of 1:1. The results of their elemental analysis are as follows:

|  | C | H | N |
|---|---|---|---|
| Analytical value: | 32.63 | 4.02 | 7.72 |
| Calculated value: (As $C_{10}H_{15}IN_2O_5$) | 32.44 | 4.08 | 7.57 |

Example 23 (Compd. No. 35)

To 44 ml of 1 N sodium hydroxide, 3.68 g of 5-bis(ethoxycarbonyl)methylene-3-cyclohexyl hydantoin was added, and the mixture was heated and reacted for one hour under reflux.

After the reaction, 276 g of iodine was added to the reaction mixture under ice-cooling, and the mixture was again heated and reacted for 4 hours under reflux.

The reaction mixture thereby obtained was filtered, and to the filtrate, 4 ml of concentrated sulfuric acid was added at room temperature, and filtered, whereupon 3.5 g (yield: 88%) of crystals of 1-cyclohexyl-5-iodoorotic acid were obtained. They were recrystallized from ethanol, whereupon yellowish needles having a decomposition point of from 239° to 240° C. were obtained as an adduct with ethanol in a molar ratio of 1:1. The results of their elemental analysis are as follows:

|  | C | H | N |
|---|---|---|---|
| Analytical value: | 38.08 | 4.67 | 6.81 |
| Calculated value: (As $C_{13}H_{19}IN_2O_5$) | 38.06 | 4.67 | 6.83 |

Example 24 (Compd. No. 36)

To 16 ml of water containing 1.1 g of 3-allyl-5-bis(ethoxycarbonyl)methylene hydantoin, 14 ml of 1 N sodium hydroxide was added at room temperature, and then the mixture was heated and reacted for one hour under reflux.

After the reaction, 1.5 ml of concentrated sulfuric acid was added to the reaction mixture at room temperature and filtered, whereupon 0.65 g (yield: 53%) of crystals of 1-allyl-5-iodoorotic acid ½ hydrate were obtained. They were recrystallized from 15 ml of water, whereupon yellow needles having a decomposition point of from 185° to 186° C. were obtained. The results of their elemental analysis are as follows:

|  | C | H | N |
|---|---|---|---|
| Analytical value: | 29.12 | 2.42 | 8.43 |
| Calculated value: (As $C_8H_7IN_2O_4 \cdot \frac{1}{2}H_2O$) | 29.02 | 2.44 | 8.46 |

Example 25 (Compd. No. 37)

To 50 ml of water containing 1.5 g of sodium 5-carboxy-1-phenylorotate monohydrate, 0.2 g of sodium hydroxide was added at room temperature, and then 1.29 g of iodine was added. The mixture was heated and reacted for 4 hours under reflux.

After the reaction, 0.5 ml of concentrated sulfuric acid was added to the reaction mixture thereby obtained at room temperature, and filtered, whereupon 1.71 g (yield: 94%) of crystals of 5-iodo-1-phenylorotic acid were obtained. They were recrystallized from ethanol, whereupon colourless needles having a decomposition point of from 258° to 260° C. were obtained as an adduct with ethanol in a molar ratio of 1:1. The results of their elemental analysis are as follows:

|  | C | H | N | I |
|---|---|---|---|---|
| Analytical value: | 38.87 | 3.24 | 6.99 | 31.65 |
| Calculated value: (As $C_{13}H_{13}IN_2O_5$) | 38.63 | 3.24 | 6.93 | 31.40 |

Example 26 (Compd. No. 37)

To 6.65 g of 5-bis(ethoxycarbonyl)methylene-3-phenyl hydantoin, 80 ml of 1 N sodium hydroxide was added at room temperature, and then the mixture was heated and reacted for one hour under reflux.

After the reaction, 5.08 g of iodine was added to the reaction mixture thereby obtained at room temperature. The mixture was heated and reacted for 4.5 hours under reflux.

After the reaction, the reaction mixture was cooled down to room temperature and then filtered, whereupon 6.92 g (yield: 97%) of crystals of 5-iodo-1-phenylorotic acid were obtained.

Example 27 (Compd. No. 38)

To 20 ml of water containing 3.62 g of 3-(p-methoxyphenyl)-5-bis(ethoxycarbonyl)methylene hydantoin, 40 ml of 1 N sodium hydroxide was added at room temperature, and then the mixture was heated and reacted for one hour under reflux.

After the reaction, 2.54 g of iodine was added at room temperature to the reaction mixture thereby obtained, and then the mixture was heated and reacted for 3 hours under reflux.

After the reaction, the reaction mixture was cooled to room temperature and filtered. To the filtrate, 20 ml of 2 N hydrochloric acid was added, whereupon crystals precipitated and 80 ml of gas was generated. The mixture was filtered, whereupon 3.3 g (yield: 85%) of crystals of 1-(p-methoxyphenyl)-5-iodoorotic acid were obtained. They were recrystallized from ethanol, whereupon yellow needles having a decomposition point of 263° C. were obtained as an adduct with ethanol in a molar ratio of 1:1. The results of their elemental analysis are as follows:

|  | C | H | N |
|---|---|---|---|
| Analytical value | 39.05 | 3.52 | 6.26 |
| Calculated value (As $C_{14}H_{15}IN_2O_6$) | 38.73 | 3.48 | 6.45 |

Example 28 (Compd. No. 39)

To 50 ml of water containing 1.65 g of sodium 5-carboxy-1-(p-chlorophenyl)orotate monohydrate, 17.5 ml of 1 N sodium hydroxide was added at room temperature, and then 1.27 g of iodine was added. Then, the mixture was heated and reacted for 7 hours under reflux.

After the reaction, the reaction mixture was cooled down to room temperature and then filtered. To the filtrate, 10 ml of 2 N hydrochloric acid was added, whereupon crystals were formed. They were filtered to obtain 1.57 g (yield: 80%) of crystals of 1-(p-chlorophenyl)-5-iodoorotic acid. They were recrystallized from ethanol, whereupon yellow fine needles having a decomposition point of from 268° to 270° C. were obtained. The results of their elemental analysis are as follows:

|  | C | H | N |
|---|---|---|---|
| Analytical value: | 33.00 | 1.93 | 7.18 |
| Calculated value: (As $C_{11}H_6ClIN_2O_4$) | 33.66 | 1.54 | 7.14 |

Example 29 (Compd. No. 39)

To 80 ml of 1 N sodium hydroxide, 7.34 g of 5-bis(ethoxycarbonyl)methylene-3-(p-chlorophenyl) hydantoin was added at room temperature, and then the mixture was heated and reacted for one hour under reflux.

After the reaction, 5.08 g of iodine was added to the reaction mixture at room temperature, and then the mixture was again heated and reacted for 5 hours under reflux.

After the reaction, the reaction mixture was cooled down to room temperature and filtered. To the filtrate, 40 ml of 2 N hydrochloric acid was added, whereupon crystals were separated. They were filtered, whereupon 6.73 g (yield: 86%) of crystals of 1-(p-chlorophenyl)-5-iodoorotic acid were obtained.

Now, Examples for the preparation of the 5-acylorotic acids will be given.

Example 30 (Compd. No. 40)

With stirring, 100 millimoles of ethyl ethoxyiminoacetate and 100 millimoles of isopropyl benzoylacetate were reacted at 100° C. for 7 hours. The reaction mixture was concentrated under reduced pressure, and 50 ml of diisopropyl ether was added to the residue and filtered, whereupon 16.8 g of crystals of 1-amino-2-benzoyl-1-ethoxycarbonyl-2-isopropoxycarbonylethylene were obtained. They were recrystallized from diisopropyl ether, whereupon 10.8 g of colourless blocks having a melting point of 106° C. were obtained.

To 70 ml of 1,2-dichloroethane containing 3.6 millimoles of tetraethylammonium fluoride, 17.8 millimoles of 1-amino-2-benzoyl-1-ethoxycarbonyl-2-(isopropoxycarbonyl)ethylene was added, and then 20 ml of 1,2-dichloroethane containing 6.5 millimoles of methyl isocyanate was dropwise added. The reaction was carried out at room temperature for 48 hours with stirring. The reaction mixture was washed with 50 ml of water, and separated. The organic layer thereby obtained was dried over anhydrous sodium sulfate and then concentrated under reduced pressure. To the residue, 50 ml of isopropyl alcohol was added and filtered, whereupon 4.22 g of crystals of 5-(benzoyl)(isopropoxycarbonyl)methylene-3-methylhydantoin were obtained. They were recrystallized from isopropyl alcohol, whereupon 3.00 g of colourless granules having a melting point of from 161° to 162° C. were obtained.

To 30 ml of ethanol containing 6.3 millimoles of 5-(benzoyl) (isopropoxycarbonyl)methylene-3-methylhydantoin, 10 ml of water containing 25.3 millimoles of potassium hydroxide was added at room temperature. Then, the reaction was carried out for one hour under reflux. To the reaction mixture, 26 ml of 1 N hydrochloric acid was added under ice-cooling, and then the mixture was concentrated under reduced pressure. To the residue, 30 ml of benzene was added, and filtered. The collected filtration product was washed with 10 ml of water, whereupon 0.59 g of crystals of 5-benzoyl-1-methylorotic acid monohydrate were obtained. They were recrystallized from water, whereupon 0.24 g of yellowish crystals having a decomposition point of from 214° to 216° C. were obtained. The results of their elemental analysis are as follows.

|  | C | H | N |
|---|---|---|---|
| Analytical value: | 53.81 | 4.11 | 9.85 |
| Calculated value: | 53.43 | 4.14 | 9.59 |

-continued

|  | C | H | N |
|---|---|---|---|
| (As $C_{13}H_{12}N_2O_6$) | | | |

Example 31 (Compd. No. 42)

With stirring, 100 millimoles of ethyl ethoxyiminoacetate and 100 millimoles of ethyl benzoylacetate were reacted at 100° C. for 5 hours. To the reaction mixture, 50 ml of cyclohexane was added and filtered, whereupon 17.8 g of crystals of 1-amino-2-benzoyl-1,2-bis(ethoxycarbonyl)ethylene were obtained. They were recrystallized from benzene, whereupon yellowish needles having a melting point of from 138° to 139° C. were obtained.

To 70 ml of 1,2-dichloroethane containing 5.9 millimoles of tetraethylammonium fluoride, 29.8 millimoles of 1-amino-2-benzoyl-1,2-bis(ethoxycarbonyl)ethylene was added, and then 59.5 millimoles of n-butyl isocyanate was dropwise added. The reaction was carried out at room temperature for 41 hours with stirring. The reaction mixture was washed with 50 ml of water, dried over anhydrous sodium sulfate, and then concentrated under reduced pressure. To the residue, 50 ml of diisopropyl ether was added and filtered, whereupon 8.25 g of crystals of 5-(benzoyl) (ethoxycarbonyl)methylene-3-n-butylhydantoin were obtained. They were recrystallized from ethanol, whereupon 5.60 g of yellowish needles having a melting point of from 142° to 144° C. were obtained. To 50 ml of water containing 10.8 millimoles of sodium hydroxide, 5.4 millimoles of 5-(benzoyl)(ethoxycarbonyl)methylene-3-n-butylhydantoin was added, and reacted at room temperature for 19 hours with stirring. To the reaction mixture, concentrated hydrochloric acid was added under ice-cooling, thereby to acidify the reaction mixture, and then filtered. The collected filtration product was washed with 100 ml of diisopropyl ether, whereupon 0.64 g of crystals of 5-benzoyl-1-n-butylorotic acid were obtained. They were recrystallized from water, whereupon 0.26 g of colourless needles having a decomposition point of from 196° to 198° C. were obtained. The results of their elemental analysis are as follows:

|  | C | H | N |
|---|---|---|---|
| Analytical value: | 60.74 | 5.30 | 8.80 |
| Calculated value: (As $C_{16}H_{16}N_2O_5$) | 60.75 | 5.10 | 8.86 |

Example 32 (Compd. No. 44)

To 80 ml of 1,2-dichloroethane containing 4.3 millimoles of tetraethylammonium fluoride, 20.0 millimoles of 1-amino-2-benzoyl-1,2-bis(ethoxycarbonyl)ethylene prepared in a manner similar to Example 31 was added, and then, 20 ml of 1,2-dichloroethane containing 80 millimoles of cyclohexyl isocyanate was dropwise added. The reaction was carried out for 5 hours under reflux. The reaction mixture was concentrated under reduced pressure. To the residue, 50 ml of diisopropyl ether was added and filtered, whereupon 6.90 g of crystals of 5-(benzoyl) (ethoxycarbonyl)methylene-3-cyclohexylhydantoin were obtained. They were recrystallized from ethanol, whereupon colourless needles having a melting point of from 184° to 186° C. were obtained.

To 20 ml of water containing 5.4 millimoles of 5-(benzoyl) (ethoxycarbonyl)methylene-3-cyclohexylhydantoin, 10 ml of water containing 10.7 millimoles of lithium hydroxide was added at room temperature. The reaction was carried out for 2.5 hours under reflux. To the reaction mixture, 11 ml of 1 N hydrochloric acid was added under ice-cooling, and then filtered, whereupon 1.08 g of crystals of 5-benzoyl-1-cyclohexylorotic acid were obtained. They were recrystallized from 90 ml of water, whereupon 0.52 g of colourless needles having a decomposition point of from 183° to 184° C. were obtained. The results of their elemental analysis are as follows:

|  | C | H | N |
|---|---|---|---|
| Analytical value: | 60.20 | 5.37 | 7.91 |
| Calculated value: (As $C_{18}H_{18}N_2O_5$) | 59.99 | 5.59 | 7.77 |

Example 33 (Compd. No. 49)

To 100 ml of 1,2-dichloroethane containing 5.3 millimoles of tetraethylammonium fluoride, 30.0 millimoles of 1-amino-2-benzoyl-1-ethoxycarbonyl-2-(isopropoxycarbonyl)ethylene was added, and then, 50 ml of 1,2-dichloroethane containing 60.0 millimoles of 3,5-dichlorophenyl isocyanate was dropwise added. The reaction was carried out for 2 hours under reflux. The reaction mixture was treated in a manner similar to Example 30, whereupon 10.76 g of colourless needles (melting point: 237° to 240° C.) of 5-(benzoyl)(isopropoxycarbonyl)methylene-3-(3,5-dichlorophenyl) hydantoin were obtained.

To 40 ml of ethanol containing 8.1 millimoles of 5-(benzoyl) (isopropoxycarbonyl)methylene-3-(3,5-dichlorophenyl)hydantoin, 10 ml of water containing 32.3 millimoles of potassium hydroxide was added at room temperature. Then, the reaction was carried out for one hour under reflux. Concentrated hydrochloric acid was added to the reaction mixture under ice-cooling, thereby to acidity the mixture, and then filtered, whereupon 4.67 g of crystals containing 5-benzoyl-1-(3,5-dichlorophenyl)orotic acid were obtained. They were washed with 120 ml of water, and then recrystallized from ethanol, whereupon 1.80 g of colourless needles having a decomposition point of from 219° to 220° C. were obtained. From the results of their elemental analysis as shown below, they were found to be an equimolar adduct of 5-benzoyl-1-(3,5-dichlorophenyl) orotic acid and ethanol.

|  | C | H | N | Cl |
|---|---|---|---|---|
| Analytical value: | 53.50 | 3.58 | 6.20 | 15.38 |
| Calculated value: (As $C_{20}H_{16}Cl_2N_2O_6$) | 53.23 | 3.57 | 6.21 | 15.71 |

Example 34 (Compd. No. 52)

With stirring, 50.0 millimoles of ethyl ethoxyiminoacetate and 500.0 millimoles of ethyl acetoacetate were reacted at 100° C. for 12 hours. The reaction mixture was concentrated under reduced pressure, whereupon 20.3 g of crystals of 1-acetyl-2-amino-1,2-bis(ethoxycarbonyl)ethylene were obtained. These crystals were recrystallized from benzene, whereupon colourless blocks having a melting point of from 88° to 89° C. were obtained.

To 80 ml of 1,2-dichloroethane containing 12.6 millimoles of tetraethylammonium fluoride, 58.9 millimoles of 1-acetyl-2-amino-1,2-bis(ethoxycarbonyl)ethylene was added, and then 20 ml of 1,2-dichloroethane containing 117.8 millimoles of ethyl isocyanate was dropwise added. The reaction was carried out for 5 hours under reflux. The reaction mixture was washed with 50 ml of water, dried over anhydrous sodium sulfate, and then concentrated under reduced pressure. To the residue, 15 ml of isopropyl alcohol was added and filtered, whereupon 9.22 g of crystals of 5-(acetyl)(ethoxycarbonyl)methylene-3-ethylhydantoin were obtained. They were recrystallized from isoropyl alcohol, whereupon yellowish crystals having a melting point of from 101° to 103° C. were obtained.

To 7.9 millimoles of 5-(acetyl) (ethoxycarbonyl)-methylene-3-ethylhydantoin, 40 ml of water containing 15.7 millimoles of lithium hydroxide was added, and the reaction was carried out for 2.5 hours under reflux. To the reaction mixture, 16 ml of 1 N hydrochloric acid was added, and the mixture was then concentrated under reduced pressure. To the residue, 50 ml of ethanol was added and filtered, whereupon 0.75 g of crystals of 5-acetyl-1-ethylorotic acid were obtained. These crystals were recrystallized from water, whereupon 0.25 g of colourless prisms having a decomposition point of from 184° to 185° C. were obtained. The results of their elemental analysis are as follows:

|  | C | H | N |
|---|---|---|---|
| Analytical value: | 47.71 | 4.41 | 12.34 |
| Calculated value: (As $C_9H_{10}N_2O_5$) | 47.79 | 4.46 | 12.38 |

Example 35 (Compd. No. 56)

To 80 ml of 1,2-dichloroethane containing 3.9 millimoles of tetraethylammonium fluoride, 20.0 millimoles of 1-acetyl-2-amino-1,2-bis(ethoxycarbonyl)ethylene prepared in a manner similar to Example 34 was added, and then 20 ml of 1,2-dichloroethane containing 50.0 millimoles of p-tolyl isocyanate was dropwise added. The reaction was carried out for one hour under reflux. To the reaction mixture, 30 ml of ethanol was added and then filtered, whereupon 5.86 g of crystals of 5-(acetyl) (ethoxycarbonyl)methylene-3-(p-tolyl)hydantoin were obtained. They were recrystallized from ethanol, whereupon 4.50 g of yellowish crystals having a melting point of from 153° to 155° C. were obtained.

To 30 ml of ethanol containing 3.8 millimoles of 5-(acetyl) (ethoxycarbonyl)methylene-3-(p-tolyl) hydantoin, 7.5 ml of water containing 15.2 millimoles of pottasium hydroxide was added at room temperature. Then reaction was carried out for one hour under reflux. To the reaction mixture, concentrated sulfuric acid was added under ice-cooling, thereby to acidify the mixture, and then filtered. The filtrate was concentrated under reduced pressure, whereupon 0.94 g of crystals of 5-acetyl-1-(p-tolyl)orotic acid were obtained. They were recrystallized from water, whereupon 0.16 g of yellowish needles having a melting point of from 224° to 226° C. were obtained. The results of their elemental analysis are as follows:

|  | C | H | N |
|---|---|---|---|
| Analytical value: | 58.22 | 4.39 | 9.55 |
| Calculated value: (As $C_{14}H_{12}N_2O_5$) | 58.33 | 4.20 | 9.72 |

Now, Test Examples will be given to establish the usefulness of the orotic acid derivatives of the present invention as agricultural germicides. In the Test Examples, the "parts" represents "parts by weight".

Test Example 1

(1) Preparation of a test emulsion

Twenty parts of the 5-haloorotic acid, 5 parts of Toxanone, and 75 parts of xylene were mixed to obtain 100 parts of an emulsion.

(2) Tests for preventing Sphaerotheca fuliginea

A cucumber plant (variety: Sagami-Hannichi Sessei) was grown in a plastic pot having a diameter of 6 cm (one plant per pot). To the young plant after 17 days from the seeding of the cucumber, the emulsion prepared by the above method (the concentration of the 5-haloorotic acid being 1000 ppm) was sprayed. Then, after drying in air, a dispersion of Sphaerotheca fuliginea (i.e. a spore dispersion prepared by brushing off conidia from the surface of a leaf diseased with Sphaerotheca fuliginea into a culture dish with use of a soft brush, and dispersing them in distilled water in a concentration of 10 spores per visual field of an optical microscope (magnification: 150 times)) was uniformly sprayed and innoculated to the yound plant. The inoculated young plant was left in an isolated glass green house, and on about the 11th day, the number of stigmas of Sphaerotheca fuliginea which appeared on the first leaf was counted. The preventive rate of the 5-haloorotic acid was calculated in accordance with the following formula for the calculation. The results thereby obtained are shown by the preventive effect indexes in Table 1.

Preventive rate (%) =

$$\left( 1 - \frac{\text{Average number of stigmas of the treated area}}{\text{Average number of stigmas of the untreated area}} \right) \times 100$$

| Preventive effect indexes | Preventing rates (%) |
|---|---|
| 5 | 91 to 100 |
| 4 | 81 to 90 |
| 3 | 61 to 80 |

TABLE 1

| Compd. No. | 5-haloorotic acids | Preventive effect indexes | Phytotoxicity |
|---|---|---|---|
| 22 | 5-chloro-1-isopropylorotic acid | 3 | None |
| 23 | 5-chloro-1-phenylorotic acid | 4 | None |
| 24 | 1-(p-methoxyphenyl)-5-chloroorotic acid | 3 | None |
| 30 | 5-bromo-1-(p-tolyl)-orotic acid | 3 | None |
| 31 | 1-(p-methoxyphenyl)-5- | 3 | None |

TABLE 1-continued

| Compd. No. | 5-haloorotic acids | Preventive effect indexes | Phytotoxicity |
|---|---|---|---|
| | bromoorotic acid | | |
| 33 | 5-bromo-1-(3,5-dichlorophenyl)orotic acid | 4 | None |
| 34 | 5-iodo-1-isopropylorotic acid | 3 | None |
| 38 | 1-(p-methoxyphenyl)-5-iodoorotic acid | 3 | None |
| 39 | 1-(p-chlorophenyl)-5-iodoorotic acid | 4 | None |
| | Molestan (Control) | 5 | None |

Test Example 2—Prevention of cucumber *Sclerotinia sclerotiorum*

(1) Preparation of test emulsions

Twenty parts of a test sample, one part of Demol, 20 parts of white carbon and 59 parts of talc were mixed and pulverized to obtain 100 parts of a wettable powder.

(2) Tests for preventing cucumber *Sclerotinia sclerotiorum*

A cucumber plant (variety: Sagami-Hanjirofushinari) was grown in a plastic pot having a diameter of 6 cm (one plant per pot). To the young plant after 2 weeks from the seeding of the cucumber, the wettable powder prepared by the above method and diluted to bring the concentration of the test sample to be 1000 ppm, was applied in an amount of 20 ml per pot. After drying in air, a cultured mycelia fragment (*Sclerotinia sclerotiorum* was cultured in a culture dish of 9 cm, and four days later, a fragment was punched out with use of a cork borer having a diameter of 7 mm at the maximum periphery) was placed at the center of the front half of the first leaf of each young plant in such a manner that the mycelia faced downward.

Then, the plant was left in an innoculation box (humidity: 100%) at 20° C. for 3 days, and the number of young plants ($n_1$ to $n_7$) diseased with *Sclerotinia sclerotiorum* in various degrees was investigated on the basis of the following standards.

Standards for evaluation of various degrees of the disease

0: plants on which no infection of the disease was observed (the number of young plants: $n_1$)
1: the length (l) of the stigma of the disease in the non-treated area $\times$ less than 0.1 (the number of young plants: $n_2$)
2: from $1 \times 0.1$ up to $1 \times 0.2$ (the number of young plants: $n_3$)
3: from $1 \times 0.2$ up to $1 \times 0.4$ (the number of young plants: $n_4$)
4: from $1 \times 0.4$ up to $1 \times 0.6$ (the number of young plants: $n_5$)
5: from $1 \times 0.6$ up to $1 \times 0.8$ (the number of young plants: $n_6$)
6: from $1 \times 0.8$ above (the number of young plants: $n_7$)

On the basis of this investigation, the preventive rates and the preventive effect indexes were obtained.

$$\text{Preventive rate (\%)} = \left[ 1 - \frac{\text{treated area } (0 \times n_1 + 1 \times n_2 + 2 \times n_3 + 3 \times n_4 + 4 \times n_5 + 5 \times n_6 + 6 \times n_7)}{\text{untreated area } (0 \times n_1 + 1 \times n_2 + 2 \times n_3 + 3 \times n_4 + 4 \times n_5 + 5 \times n_6 + 6 \times n_7)} \right] \times 100$$

| Preventive effect indexes | Preventing rates (%) |
|---|---|
| 5 | 91 to 100 |
| 4 | 81 to 90 |
| 3 | 61 to 80 |

The results are shown below:

| Compound Nos. | Test samples | Preventive effect indexes | Phytotoxicity |
|---|---|---|---|
| 1 | $K^+ H_3^+$ [i-Pr-N-C(=O)-C(COO$^-$)=C(COO$^-$)-N(H)-C(=O)] · H$_2$O | 3 | None |
| 15 | $Na^+ H_3^+$ [Cl-C$_6$H$_4$-N-C(=O)-C(COO$^-$)=C(COO$^-$)-N(H)-C(=O)] · H$_2$O | 3 | None |

| Compound Nos. | Test samples | Preventive effect indexes | Phytotoxicity |
|---|---|---|---|
| 20 | $K^+H_3^+$ [2,4,5-trichlorophenyl pyrimidine dicarboxylate structure] | 3 | None |
| 40 | [CH$_3$-N pyrimidine with COPh and COOH structure] | 3 | None |
| 46 | [Ph-N pyrimidine with COPh and COOH structure] | 4 | None |

Test Example 3—Test for controlling bacterial leaf blight (submerged application)

(1) Preparation of Wettable Test Samples

Twenty parts of a test sample, one part of DEMOL, 20 parts of white carbon and 59 parts of talc were mixed and pulverized to obtain 100 parts of a wettable sample.

(2) Controlling Test

Paddy-field rice seeds (variety: Nihonbare) were seeded in a synthetic resin pot having a diameter of 6 cm (5 seeds per pot), and cultivated in a glass green house. Rice plants of from 5.5 to 6.5 leaf stage were subjected to the test. The wettable sample prepared according to the above mentioned method was diluted with water to have a concentration of the test sample being 500 ppm, and 3 ml of the diluted sample was applied in a submerged application manner. After the application, the pot was left for 2 days in the glass green house to permit the sample to be adequately absorbed from the root, and then the inoculation was conducted. The inoculum was prepared by culturing bacterial leaf blight bacteria (*Xanthomonas oryzeae*) in a SUWA liquid culture medium at 28° C. for 48 hours by shake culture and by adjusting the concentration so that there were $10^{7-8}$ bacteria per ml. The inoculation was made into the leaf blades of the upper two leaves by a double needle inoculation avoiding the inoculation to the mid-vein. After the inoculation, the plants were kept in the glass greenhouse. Two weeks after the inoculation, the number of rice plants ($n_1$ to $n_7$) diseased with bacterial leaf blight was counted for the respective degrees of disease according to the following evaluation standard. The number of test plants was 30 plants in each area.

Evaluation standards (preventive effect indexes) for the diseased degrees

0: No disease was observed (number of rice plants: $n_1$)

1: Slight disease was observed (number of rice plants: $n_2$)

2: A lesion of not greater than 1 cm was observed (number of rice plants: $n_3$)

3: A lesion of not greater than 2 cm was observed (number of rice plants: $n_4$)

4: A lesion of not greater than 5 cm was observed (number of rice plants: $n_5$)

5: A lesion of not greater than 10 cm was observed (number of rice plants: $n_6$)

6: A lesion of greater than 10 cm was observed (number of rice plants: $n_7$)

The results thereby obtained are shown below.

| Compound Nos. | Test samples | Preventive effect indexes | Phytotoxicity |
|---|---|---|---|
| 20 | $K^+H_3^+$ [2,4,5-trichlorophenyl pyrimidine dicarboxylate structure] | 3 | None |
| 58 | [dichlorophenyl-N pyrimidine with COCH$_3$ and COOH structure] | 4 | None |
| 43 | [CH$_2$=CHCH$_2$-N pyrimidine with COPh and COOH structure] | 3 | None |

| Compound Nos. | Test samples | Preventive effect indexes | Phytotoxicity |
|---|---|---|---|
| 44 | 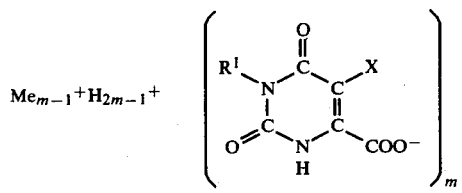 | 4 | None |
| 38 | 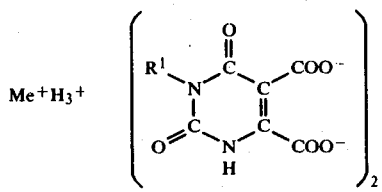 | 3 | None |

What is claimed is:

1. An orotic acid derivative represented by the general formula

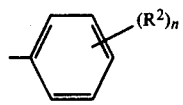

where Me is an alkali metal, $R^1$ is an alkyl group of from 1 to 4 carbon atoms, an allyl group, a cyclohexyl group, a benzyl group, or a group $$\underset{}{\phantom{XX}}\!\!\!-\!\!\!\bigcirc\!\!\!-(R^2)_n$$

(where $R^2$ is an alkyl group of from 1 to 4 carbon atoms, an alkoxyl group of from 1 to 4 carbon atoms or a halogen atom and n is an integer of 0, 1, 2 or 3), m is an integer of 1 or 2, and X is a chlorine atom, a bromine atom, an iodine atom or —$COR^0$ (where $R^0$ is an alkyl group of from 1 to 4 carbon atoms or a phenyl group) when m is 1, and a group —$COO^-$ when m is 2.

2. The orotic acid derivative as claimed in claim 1, which is represented by the formula $$Me^+H_3^+ \left\{ \text{structure} \right\}_2$$

where Me and $R^1$ are as defined in claim 1.

3. The orotic acid derivative as claimed in claim 1, which is represented by the formula

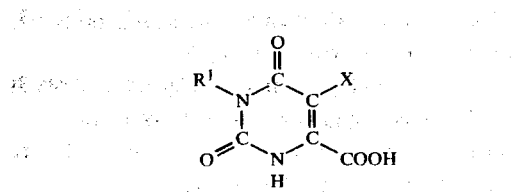

where $R^1$ and X are as defined in claim 1.

4. The orotic acid derivative as claimed in claim 2, which is selected from the group consisting of potassium 5-carboxy-1-isopropylorotate, sodium 5-carboxy-1-(n-butyl)orotate, lithium 5-carboxy-1-(n-butyl) orotate, potassium 5-carboxy-1-allylorotate, potassium 5-carboxy-1-cyclohexylorotate, sodium 5-carboxy-1-cyclohexylorotate, potassium 5-carboxy-1-phenylorotate, lithium 5-carboxy-1-phenylorotate, potassium 5-carboxy-1-(p-tolyl)orotate, sodium 5-carboxy-1-(p-tolyl)orotate, potassium 5-carboxy-1-(2,5-dichlorophenyl)orotate, sodium 5-carboxy-1-(3,5-dicholorophenyl)orotate, lithium 5-carboxy-1-(3,5-dichlorophenyl)orotate, potassium 5-carboxy-1-(2,4,5-trichlorophenyl)orotate, and sodium 5-carboxy-1-(p-methoxyphenyl)orotate.

5. The orotic acid derivative as claimed in claim 2, which is potassium 5-carboxy-1-(n-butyl)orotate.

6. The orotic acid derivative as claimed in claim 2, which is potassium 5-carboxy-1-benzylorotate.

7. The orotic acid derivative as claimed in claim 2, which is sodium 5-carboxy-1-phenylorotate.

8. The orotic acid derivative as claimed in claim 2, which is lithium 5-carboxy-1-(p-tolyl)orotate.

9. The orotic acid derivative as claimed in claim 2, which is sodium 5-carboxy-1-(p-chlorophenyl)orotate.

10. The orotic acid derivative as claimed in claim 2, which is potassium 5-carboxy-1-isopropylorotate.

11. The orotic acid derivative as claimed in claim 2, which is potassium 5-carboxy-1-(2,4,5-trichlorophenyl)orotate.

12. The orotic acid derivative as claimed in claim 3, which is selected from the group consisting of 5-chloro-1-isopropylorotic acid, 5-chloro-1-phenylorotic acid, 1-(p-methoxyphenyl)-5-chloroorotic acid, 5-chloro-1-(p-chlorophenyl)orotic acid, 5-bromo-1-isopropylorotic acid, 5-bromo-1-(n-butyl)orotic acid, 1-benzyl-5-bromoorotic acid, 5-bromo-1-phenylorotic acid, 5-bromo-1-(p-tolyl)orotic acid, 1-(p-methoxyphenyl)-5-bromoorotic acid, 5-bromo-1-(p-chlorophenyl)orotic acid, 5-bromo-1-(3,5-dichlorophenyl)orotic acid, 5-iodo-1-isopropylorotic acid, 1-cyclohexyl-5-iodoorotic acid, 1-allyl-5-iodoorotic acid, 5-iodo-1-phenylorotic acid, 1-(p-methoxyphenyl)-5-iodoorotic acid, 1-(p-chlorophenyl)-5-iodoorotic acid, 5-benzoyl-1-isopropylorotic acid, 5-benzoyl-1-n-butylorotic acid, 5-benzoyl-1-benzylorotic acid, 5-benzoyl-1-(p-tolyl)orotic acid, 5-benzoyl-1-(3,4-xylyl)orotic acid, 5-benzoyl-1-(3,5-dichlorophenyl)orotic acid, 5-benzoyl-1-(2,4,5-trichlorophenyl)orotic acid, 5-benzoyl-1-(p-methoxyphenyl)orotic acid, 5-acetyl-1-ethylorotic acid, 5-acetyl-1-(n-butyl)orotic acid, 5-acetyl-1-phenylorotic acid, 5-acetyl-1-cyclohexylorotic acid, 5-acetyl-1-(p-tolyl)orotic acid, 5-acetyl-1-(p-chlorophenyl)orotic acid, 5-acetyl-1-(3,5-dichlorophenyl)orotic acid and 5-acetyl-1-(p-methoxyphenyl)orotic acid.

13. The orotic acid derivative as claimed in claim 3, which is 5-chloro-1-isopropylorotic acid.

14. The orotic acid derivative as claimed in claim 3, which is 5-chloro-1-phenylorotic acid.

15. The orotic acid derivative as claimed in claim 3, which is 1-(p-methoxyphenyl)-5-chloroorotic acid.

16. The orotic acid derivative as claimed in claim 3, which is 5-bromo-1-(p-tolyl)orotic acid.

17. The orotic acid derivative as claimed in claim 3, which is 1-(p-methoxyphenyl)-5-bromoorotic acid.

18. The orotic acid derivative as claimed in claim 3, which is 5-bromo-1-(3,5-dichlorophenyl)orotic acid.

19. The orotic acid derivative as claimed in claim 3, which is 5-iodo-1-isopropylorotic acid.

20. The orotic acid derivative as claimed in claim 3, which is 1-(p-methoxyphenyl)-5-iodoorotic acid.

21. The orotic acid derivative as claimed in claim 3, which is 1-(p-chlorophenyl)-5-iodoorotic acid.

22. The orotic acid derivative as claimed in claim 3, which is 5-benzoyl-1-methylorotic acid.

23. The orotic acid derivative as claimed in claim 3, which is 5-benzoyl-1-phenylorotic acid.

24. The orotic acid derivative as claimed in claim 3, which is 5-acetyl-1-(3,5-dichlorophenyl)orotic acid.

25. The orotic acid derivative as claimed in claim 3, which is 5-benzoyl-1-allylorotic acid.

26. The orotic acid derivative as claimed in claim 3, which is 5-benzoyl-1-cyclohexylorotic acid.

* * * * *